United States Patent

Daum et al.

[11] 4,265,893
[45] May 5, 1981

[54] DIURETIC COMPOSITIONS

[75] Inventors: Adam Daum, Basel, Switzerland; Michel Fernex, Biederthal; Alexander E. Wick, Le Mesnil-le Roy, both of France

[73] Assignee: Hoffmann-La Roche Inc., Nutley, N.J.

[21] Appl. No.: 72,771

[22] Filed: Sep. 5, 1979

[30] Foreign Application Priority Data

Sep. 12, 1978 [CH] Switzerland .......... 9547/78

[51] Int. Cl.³ .......... A61K 31/54; A61K 31/505
[52] U.S. Cl. .......... 424/246; 424/251
[58] Field of Search .......... 424/251, 246

[56] References Cited

FOREIGN PATENT DOCUMENTS 2443682  3/1975  Fed. Rep. of Germany .

Primary Examiner—Stanley J. Friedman
Attorney, Agent, or Firm—Jon S. Saxe; Bernard S. Leon; William G. Isgro

[57] ABSTRACT

A composition having diuretic activity which contains a potassium-flushing diuretic and a potassium-retaining compound, said potassium-retaining compound is a compound of the formula

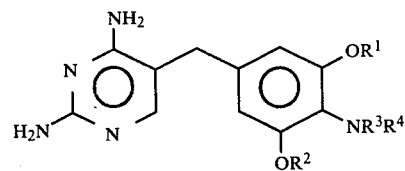

wherein $R^1$ and $R^2$ are $C_{1-6}$-alkyl or $C_{2-6}$-alkenyl, and $R^3$ and $R^4$, independently, are hydrogen, $C_{1-6}$-alkyl, $C_{2-6}$-alkenyl or $C_{1-6}$-acyl, or $R^3$ and $R^4$ together with the nitrogen atom are an optionally unsaturated 5-, 6- or 7-membered heterocyclic group, or a physiologically compatible salt thereof, are described.

4 Claims, No Drawings

DIURETIC COMPOSITIONS

BRIEF SUMMARY OF THE INVENTION

The invention relates to a composition having diuretic activity which comprises a potassium-flushing diuretic agent and a potassium-retaining compound, said potassium-retaining compound is a compound of the formula

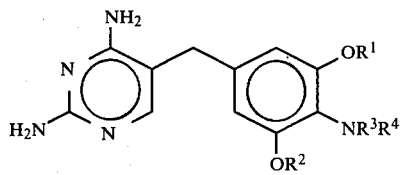

wherein $R^1$, $R^2$, $R^3$ and $R^4$ are as hereinafter described, or a physiologically compatible salt thereof.

DETAILED DESCRIPTION OF THE INVENTION

The group of orally active sulfonamides of the thiazide type, that is, benzothiadiazine derivatives, such as, hydrochlorothiazide and hydroflumethiazide, and thiazide analogs, such as, quinethazone, chlorthalidone and mefruside, represents the diuretics which are most frequently prescribed at the present time. These diruetics are, however, not free from undesirable side-effects attributable to an increased potassium excretion in the patient and which can manifest themselves, for example, as anorexia, illness, weakness or fatigue. The potassium loss is particularly pronounced at the beginning of therapy, primarily when the diuresis is strong and one adheres to a strict diet. As a rule, a potassium salt, particularly potassium chloride, is prescribed for the patient in order to compensate for the potassium loss. On the other hand, potassium-retaining diuretics which acts as aldosterone antagonists, for example, spironolactone, or pseudo-aldosterone antagonists, for example, triamterene, are known. However, these diuretics give rise to the retention of potassium. Spironolactone and triamterene are mainly administered in combination with thiazides or other diuretics (F. H. Meyers et al., Lehrbucgh der Pharmakologie, Springer-Verlag, 1975, p. 178–189 and 768).

Surprisingly, it has now been found, in accordance with the invention, that certain p-aminobenzylpyrimidine derivatives also possess a pronounced potassium-retaining action. The referred-to p-aminobenzylpyrimidine derivatives are compounds of the formula

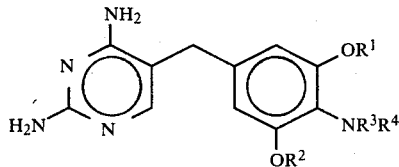

wherein $R^1$ and $R^2$ are $C_{1-6}$-alkyl or $C_{2-6}$-alkenyl and $R^3$ and $R^4$, independently, are hydrogen, $C_{1-6}$-alkenyl, $C_{2-6}$-alkenyl or $C_{1-6}$-acyl, or $R^3$ and $R^4$ together with the nitrogen atom to which they are attached are an optionally unsaturated 5-, 6- or 7-membered heterocyclic group, and their physiologically compatible salts.

With respect to the aforementioned p-aminobenzylpyrimidine derivatives, it was previously known only that they possessed antibacterial activity and potentiated the activity of antibacterially active sulfonamides, see, for example, German Offenlegungsschrift No. 2,443,682. It has now been shown that the compounds of formula I and their physiologically compatible salts demonstrate advantages vis-a-vis already known potassium-retaining diuretics and, therefore, they can be utilized as potassium-retaining agents in combination with diuretics which induce an increased potassium excretion.

The invention relates to the foregoing finding, and accordingly, is concerned with pharmaceutical preparations or compositions having diuretic activity which contain a potassium-flushing diuretic compound and a potassium-retaining compound, said potassium-retaining compound is a compound of formula I hereinbefore described or a physiologically compatible salt thereof. The invention is also concerned with the method of using the compounds of formula I and their physiologically compatible salts to reduce potassium excretion, particularly in combination with potassium-flushing diuretics.

Exemplary of $C_{1-6}$-alkyl groups are methyl, ethyl, propyl, n-butyl, isobutyl, tert.butyl, hexyl, and the like. Exemplary of $C_{2-6}$-alkenyl groups are vinyl, allyl, and the like. $C_{1-6}$-acyl groups are preferably derived from aliphatic carboxylic acids, such as formic acid, acetic acid, propionic acid, butyric acid, ethoxyacetic acid, and the like, and are exemplified by the groups, such as, lower alkanoyl of 1 to 7 carbon atoms, for example, formyl, acetyl, propionyl, butyryl, ethoxyacetyl, and the like. When $-NR^3R^4$ is an optionally unsaturated 5-, 6- or 7-membered heterocycle or heterocyclic group, it can be, for example, pyrrolo, pyrrolino, pyrrolidino, piperidino or azepino.

A preferred group of compounds of formula I comprises compounds wherein $R^1$ and $R^2$ each are $C_{1-3}$-alkyl and $R^3$ and $R^4$ each are hydrogen or $C_{1-3}$-alkyl, or $R^3$ and $R^4$ taken together with the nitrogen atom to which they are attached, are a 5- to 7-membered saturated heterocyclic group. Another preferred group of compounds of formula I comprises compounds wherein $R^1$ and $R^2$ are methyl and $R^3$ and $R^4$, independently, are hydrogen, methyl, ethyl or formyl, or $R^3$ and $R^4$ together with the nitrogen atom to which they are attached are pyrrolidino. An especially preferred compound of formula I is 2,4-diamino-5-(4-amino-3,5-dimethoxybenzyl)-pyrimidine.

Physiologically compatible salts of the compounds of formula I comprise all salts which are customary and familiar to a person skilled in the art and which are formed with organic or inorganic acids, such as, hydrochloric acid, sulfuric acid, phosphoric acid, formic acid, acetic acid, oxalic acid, tartaric acid, maleic acid, benzoic acid, succinic acid, fumaric acid, levulinic acid, salicylic acid, citric acid, isocitric acid, adipic acid, lactic acid, α-ketoglutaric acid, malic acid, malonic acid, glyceric acid, mevalonic acid, glucuronic acid, neuraminic acid, glutaric acid, glucaric acid, aspartic acid, gluconic acid, mandelic acid, ascorbic acid, lactobionic acid, glucoheptonic acid, glutamic acid, nicotinic acid, pantothenic acid, folic acid, adenylic acid, geranylic acid, cytidylic acid, inosic acid or the like.

In the pharmaceutical preparations or compositions provided by the invention, the p-aminobenzylpyrimidine derivatives aforesaid can be combined with any diuretic which brings about potassium-flushing. The latter diuretics are primarily strong acting diuretics of the thiazide type and analogs thereof, such as, hydrochlorothiazide, hydroflumethiazide, trichlormethiazide, thiabuzide, polythiazide, cyclopenthiazide and quinethazone, but there also come into consideration diuretics which have the aforementioned side-effects but do not belong to the thiazide type diuretic, for example, ethacrynic acid.

The pharmaceutical preparations or compositions provided by the invention contain besides the active ingredients, which can be liberated directly or with delay, the customary inert organic or inorganic carrier materials suitable for oral or parenteral administration, especially the customary carrier materials for tablets, dragees, capsules or injection solutions, as well as, if desired, adjuvants such as preserving, stabilizing, wetting or emulsifying agents, flavor-improving agents, salts for varying the osmotic pressure or buffer substances. The pharmaceutical preparations or compositions of the invention can be prepared in a manner familiar to a person skilled in the art by mixing the active ingredients with suitable inert organic or inorganic carrier materials and thereafter, compounding the mixture into a galenical form convenient for oral or parenteral administration.

With the aforementioned p-aminobenzylpyrimidine derivatives there can be achieved a very high, in some instances up to 90%, maximum potassium retention, which permits a relatively small daily dosage. Such daily dosage conveniently is in the range of from about 1 mg. to 20 mg, preferably in the range of from about 5 to 10 mg. The dose present in the pharmaceutical preparations or compositions of the invention is, however, determined primarily by the amount of the potassium loss brought about by the diuretically active component. Per administration unit or dosage unit, the dose can likewise be 1-20 mg. For the diuretic treatment of warm-blooded animals, the dosage at which the preparation or composition is administered is adjusted to the rate of the weight loss and to the serum electrolyte titres of the patient and is supervised and determined by the person administering or directing the administration of the composition of the invention. The optimum dosage depends on the serum potassium level.

The following Example illustrates the present invention:

EXAMPLE

Tablets containing the following ingredients were prepared:

| | | |
|---|---|---|
| 1. | 2,4-Diamino-5-(4-amino-3,5-dimethoxy-benzyl)-pyrimidine | 10.0 mg. |
| 2. | Hydrochlorothiazide | 50.0 mg. |
| 3. | D-Mannitol | 43.0 mg. |
| 4. | Maize Starch | 50.0 mg. |
| 5. | Polyvinylpyrrolidone | 5.0 mg. |
| 6. | Talc | 1.5 mg. |
| 7. | Magnesium stearate | 0.5 mg. |
| | -continued | 160.0 mg. |

Ingredients 1-3 and 80% of ingredient 4 were passed through a sieve, mixed and then treated and granulated with a sufficient amount of rectified alcohol and water as well as ingredient 5. The granulate was dried, passed through a sieve, and after being mixed with the remaining ingredients, pressed into tablets weighing 160.0 mg. and having a break-bar.

We claim:

1. A method of inducing diuresis which comprises administering a composition which contains a diuretically effective amount of a potassium-flushing diuretic agent selected from the group consisting of hydrochlorothiazide, hydroflumethiazide, trichlormethiazide, thiabuzide, polythiazide, cyclopenthiazide, quinethazone, and ethacrynic acid and an amount in the range of from about 1 mg to 20 mg of a potassium-retaining compound, said potassium-retaining compound is a compound of the formula wherein $R^1$ and $R^2$ are $C_{1-6}$-alkyl, and $R^3$ and $R^4$, independently, are hydrogen, or a physiologically compatible salt thereof.

2. A composition having diuretic activity which comprises a diuretically effective amount of a potassium-flushing diuretic agent selected from the group consisting of hydrochlorothiazide, hydroflumethiazide, trichlormethiazide, thiabuzide, polythiazide, cyclopenthiazide, quinethazone and ethacrynic acid and an amount in the range of from about 1 mg to 20 mg of a potassium-retaining compound, wherein said potassium-retaining compound is a compound of the formula wherein $R^1$ and $R^2$ are $C_{1-6}$-alkyl; and $R^3$ and $R^4$, independently, are hydrogen, or a physiologically compatible salt thereof.

3. A composition in accordance with claim 2, wherein the compound of formula I is 2,4-diamino-5-(4-amino-3,5-dimethoxybenzyl)-pyrimidine.

4. A composition in accordance with claim 3, wherein the potassium-flushing diuretic is hydrochlorothiazide.

* * * * *